United States Patent
Lai

(10) Patent No.: US 10,401,288 B2
(45) Date of Patent: Sep. 3, 2019

(54) SYSTEM AND/OR METHOD OF SEPARATING MULTIPLE FLUORESCENT-DYE COLOR SIGNALS

(75) Inventor: Ching Ming Lai, Wakefield, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 1976 days.

(21) Appl. No.: 13/076,576

(22) Filed: Mar. 31, 2011

(65) Prior Publication Data

US 2012/0248297 A1    Oct. 4, 2012

(51) Int. Cl.
*G01N 33/48* (2006.01)
*G01N 21/64* (2006.01)
*G06G 7/58* (2006.01)

(52) U.S. Cl.
CPC .............................. *G01N 21/6408* (2013.01)

(58) Field of Classification Search
None
See application file for complete search history.

*Primary Examiner* — Eric S Dejong
(74) *Attorney, Agent, or Firm* — TraskBritt

(57) ABSTRACT

A method comprises receiving an output signal of one of multiple detection channels. The method further includes color separating the output signal and generating a color-separated signal substantially only with the peaks corresponding to the detected signals with the principle emission in the emission spectrum range of the detection channel. The method further includes estimating a time-variant amplitude of the gradually decaying tail and removing the time-variant amplitude from the color-separated signal. The method further includes generating a corrected colored-separated signal with substantially only the peaks corresponding to the fluorescent dyes attached to the fragments in the sample.

23 Claims, 8 Drawing Sheets

SYSTEM AND/OR METHOD OF SEPARATING MULTIPLE FLUORESCENT-DYE COLOR SIGNALS

TECHNICAL FIELD

The following generally relates to color separating multiple color signals and finds particular application to DNA analysis. However, the following is also amenable to other applications.

BACKGROUND

DNA genotyping is the process of determining the sequence of DNA nucleotides at a position on a locus (a chromosome of a gene or other chromosome marker). For the purpose of identifying a human, certain generic loci have been selected as the standard markers to characterize the DNA. Each marker is a DNA fragment containing a repetition of a certain nucleotide sequence. Generally, there are thirteen (13) cores and several other accepted standard markers by the security authorities. These markers contain short repetitions (e.g., roughly from five (5) to forty (40)) of four nucleotides referred to as a Short Tandem Repeat (STR).

The repetition numbers at these markers vary randomly from person to person. The specific form of the DNA sequence at a generic locus is called an allele, which provides sufficient differentiation among people. The STR sequence is inherited from parent's DNA. At each marker, there may be two different alleles, one from each parent, and it is called heterozygous. If the alleles from both parents have same STR numbers, it is homozygous. If the alleles of 13 core markers were heterozygous, each person will have twenty-six (26) different allele numbers. Assume each number is evenly distributed over a range of ten (10), the likelihood of having two people with the same alleles numbers from these thirteen (13) markers is extremely small.

A DNA analyzer has been used to determine allele numbers in DNA samples. For this, the DNA sample is introduced into a micro-channel of a rigid sample carrier called a biochip, which generally includes multiple micro-channels in parallel to process multiple samples simultaneously. A DNA fragment containing all STR nucleotides and adjacent sections of nucleotides at each locus is copied from the DNA sample, and replicated through polymerase chain reaction (PCR). The fragments are labeled with target specific fluorescent dyes (or fluorophores) that emit radiation having different principle emission spectra in response to being excited by light. The labeled fragments are separated by size through electrophoresis.

The fragment size is measured in the unit of base pairs (e.g., 100 to 400), where a base pair is the size of a pair of DNA nucleotides. The separated fragments are excited by an excitation light. In response thereto, the dyes emit their characteristic radiation. A detection system includes multiple detection channels, each configured to detect radiation having emission spectra in a different emission spectrum range corresponding to a different one of the dyes. The channels detect the emission spectra and output signals with peaks indicative thereof. The peaks are used to locate fragments in the signal, the peak detection time determines the fragment size, and the fragment size identifies the locus of the fragment and is used to identify it as a DNA fragment in the locus with known STR number.

Unfortunately, the emission spectra of the dyes partially overlap. As a result, a detection channel output signal will include peaks originating from dyes attached to fragments and with principle emission corresponding to the detection channel and peaks originating from dyes attached to fragments and with principle emission corresponding to other detection channels. This has been referred to as color-bleed. The output signal will also include a cluster peak of free dye peaks in which free dyes are dyes that are not attached to any fragment. The detection channel output signal will also include an offset signal including an optical and detection system offset and background signals from fluorescent emission from the sample carrier and non-fluorescent excitation light scatter.

FIG. 1 shows an example portion of an output signal 102 of one of the detection channels. In FIG. 1, a y-axis 104 represents signal amplitude and an x-axis 106 represents time. The output signal 102 includes peaks 108 and 110, which originate from dyes attached to fragments and with principle emission corresponding to detection channel, peaks 112 and 114, which originate from other dyes attached to other fragments and with principle emission corresponding to other detection channels, a cluster peak 116, which is an superposition of the free dye peaks, and an offset signal 118 representing optical and detection system offset and background signals. As shown, the cluster peak 116 has a tail 120 that gradually decays over time and adds to and raises the amplitudes of the peaks 108-114, and the offset signal 118 raises the amplitudes of the cluster peak 116 and the peaks 108-114.

The raised amplitudes of the peaks 108-114 may introduce error in the color separation process. One approach to attempt to return the amplitudes back to their pre-raised state has been to measure the offset signal 118 and the cluster peak 116 and subtract them from the output signal 102. FIG. 2 shows an example signal 202 which is the output signal 102 (FIG. 1) with a measured offset signal 118 and cluster peak 116 subtracted there from. As shown, the example signal 202 includes the peaks 108-114 and a portion 204 of the cluster peak 116, which was not fully removed in this example. Unfortunately, it is difficult to accurately measure the tail 120 of the cluster peak 116, especially in the presence of the peaks 108-114. Consequently, the amplitudes of the peaks 108-114 in the example signal 202 may deviate from their true amplitudes.

As the result, the color separation process may introduce pull-up (positive or negative (pull-down)) artifact into the color-separated signals, even with accurate color bleed factors. FIG. 3 shows an example of such artifact for three color-separated fragments and five dyes. In FIG. 3, each signal 302, 304, 306, 308 and 310 represents a different dye. A first fragment peak 312 corresponds to the signal 304, is measured accurately, and does not introduce artifact into the other signals. A second fragment peak 314 corresponds to the signal 306, includes error, and introduces pull-up artifact 316, 318, 320 and 322 into the other signals. A third fragment peak 324 corresponds to the signal 304, includes error, and introduces pull-up artifacts 330 and 332 in signals 308 and 310 and pull-down artifacts 326 and 328 in signals 302 and 306.

Pull-up and pull-down artifacts can be detrimental to identifying fragments from the signals 302-310. That is, pull-up artifact may lead to false peaks being identified as true peaks (e.g., by pull-up artifact of sufficient amplitude) in the color-separated signals, and pull-down artifact may lead to true peaks being suppressed (e.g., by pull-up artifact of sufficient negative amplitude) from the color-separated signals and missed. The foregoing adds uncertainty in the detection and identification of fragments in the sample and, thus, determining STR numbers in DNA samples. Furthermore, the nature of the pull-up artifact makes it difficult to effectively and reliably perform a correction for the artifact after color separation, and such a correction can substantially distort the signal, which can further add to the uncertainty.

Therefore, there is an unresolved need for other approaches to removing the tail 120 of the cluster peak 116 from the peaks 108 and 110, without introducing or reducing pull-up artifact into the color-separated signals.

SUMMARY

Aspects of the application address the above matters, and others.

In one aspect, a method includes color separating peaks in signals output by multiple detection channels that respectively are configured to detect signals with emission spectra in different predetermined emission spectrum ranges and to generate signals indicative thereof. The method includes receiving an output signal of one of the detection channels. The output signal includes peaks corresponding to detected signals with principle emission spectra in the emission spectrum range of the detection channel and peaks corresponding to detected signals with principle emission spectra in the emission spectrum range of one or more of the other detection channels and with emission spectra that overlaps the emission spectrum range of the detection channel. The method further includes color separating the output signal and generating a color-separated signal substantially only with the peaks corresponding to the detected signals with the principle emission in the emission spectrum range of the detection channel. The color-separated signal includes peaks corresponding to fluorescent dyes attached to fragments in a sample and a cluster peak corresponding to fluorescent dyes that are not attached to fragments in the sample, and wherein the cluster peak includes a gradually decaying tail with a time-variant amplitude that adds to and raises amplitudes of the peaks corresponding to the fluorescent dyes attached to the fragments in the sample. The method further includes estimating the time-variant amplitude of the gradually decaying tail and removing the time-variant amplitude from the color-separated signal and generating a corrected colored-separated signal with substantially only the peaks corresponding to the fluorescent dyes attached to the fragments in the sample.

In another aspect, a sample processing system includes a color separator that color separates a detection channel output signal, generating a color-separated signal, a time-variant baseline signal determiner that determines a time-variant amplitude of a baseline signal of the color-separated signal, a time-variant baseline signal remover that removes the determined time-variant amplitude from the color-separated signal, generating a corrected color-separated signal.

In another aspect, a computer readable storage medium with computer executable instructions embedded thereon, which, when executed by a processor, cause the processor to: measure an amplitude of a time-invariant offset to an output signal of a detection channel of a plurality of detection channels processing a DNA sample and removing the amplitude from the output signal generating a time-invariant offset corrected signal, coloring separating the time-invariant offset corrected signal generating a color-separated signal, and determining an amplitude of a time-variant offset to the color-separated signal and removing the amplitude from the color-separated signal generating a corrected color-separated signal.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
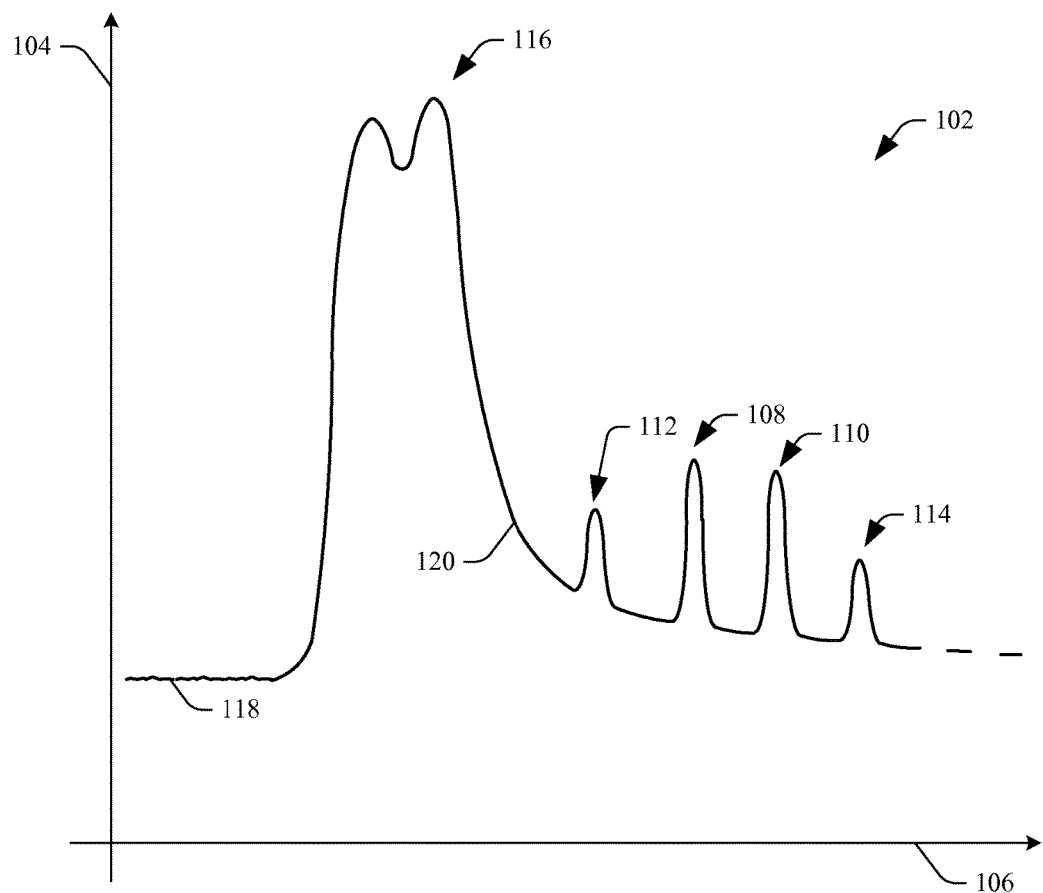
FIG. 1 illustrates an example output signal of a detection channel.
Figure 2:
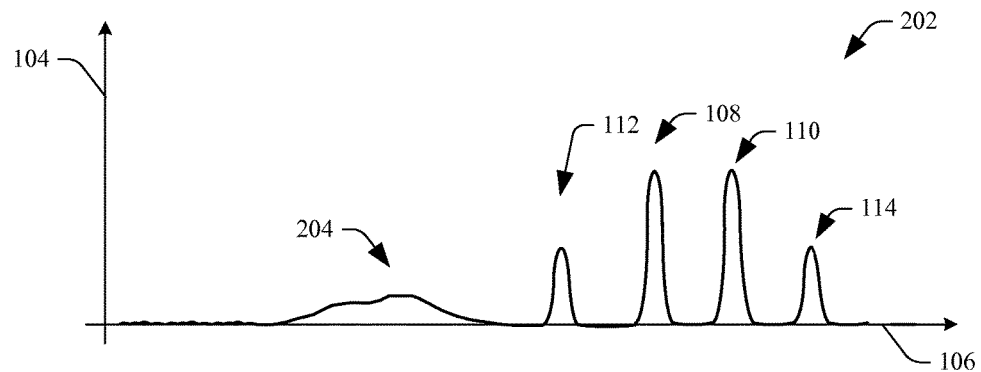
FIG. 2 illustrates the output signal of FIG. 1 with most of the cluster peak and tail and the offset and background signals removed based on a prior art approach.
Figure 3:
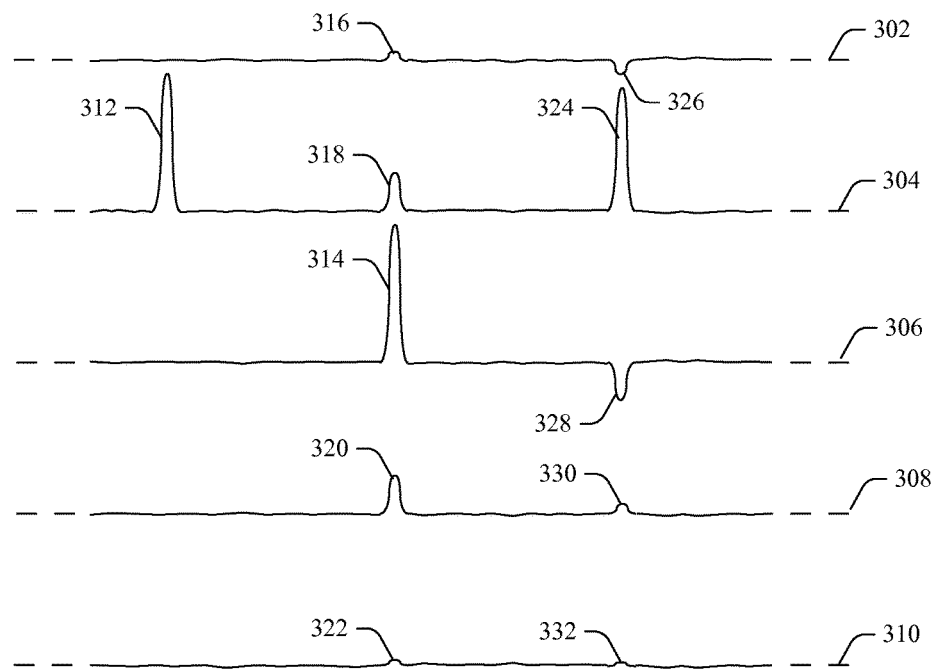
FIG. 3 illustrates example color-separated signals with pull-up artifact for the output signal of FIG. 2.
Figure 4:
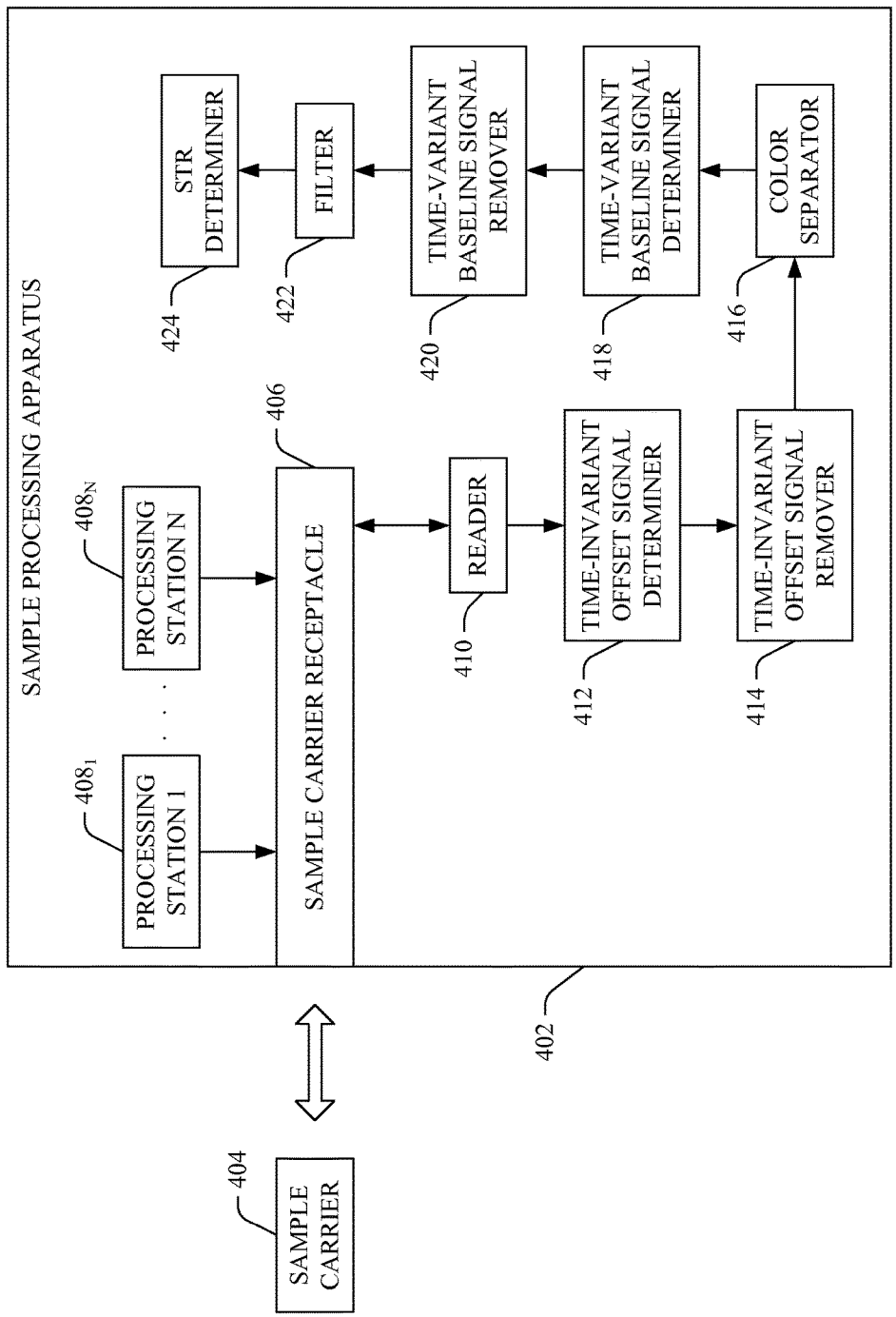
FIG. 4 schematically illustrates an example sample processing apparatus.

FIG. 4 illustrates a sample processing apparatus 402 configured for processing one or more samples carried by a sample carrier 404.

A suitable sample carrier 404 includes, but is not limited to, a biochip, a lab-on-a-chip, and/or other sample carrier. Such a sample carrier 404 may include one or more microchannels for carrying and moving, in parallel and/or in series, one or more samples through a plurality of different processing regions of the sample carrier 404. Suitable samples include, but are not limited to, a bio-sample (e.g., saliva, blood, skin cells, and/or other bio-material), a non-bio sample, etc. The sample processing apparatus 402 includes a sample carrier receptacle 406 configured to receive the sample carrier 404 for processing the sample(s) carried thereby.

The sample processing apparatus 402 further includes one or more processing stations $408_1, \ldots, 408_N$ (wherein N is an integer equal to or greater than one), collectively referred to herein as processing stations 408, configured to process samples carried by the sample carrier 404 when the sample carrier 404 is inserted in the sample carrier receptacle 406. Such processing may includes processing DNA samples. In this instance, the processing stations 408 may be configured to extract and purify DNA fragments from the sample, replicate and label the DNA fragments with fluorescent dyes having known principle emission spectra (color), and separate the labeled fragments based on fragment size via electrophoresis.

The sample processing apparatus 402 also includes an optical reader 410. The optical reader 410 includes a light source that directs an excitation light beam of a predetermined wavelength range at the separated fragments. In one instance, the light source emits a 488 nm relatively narrow light beam with a diameter in the order of ten (10) to one hundred (100) microns. In another instance, the light source emits a light beam with a different wavelength, and/or with a different diameter. Examples of suitable light sources include, but are not limited to, a laser, a light emitting diode (LED), and the like.

Figure 5:
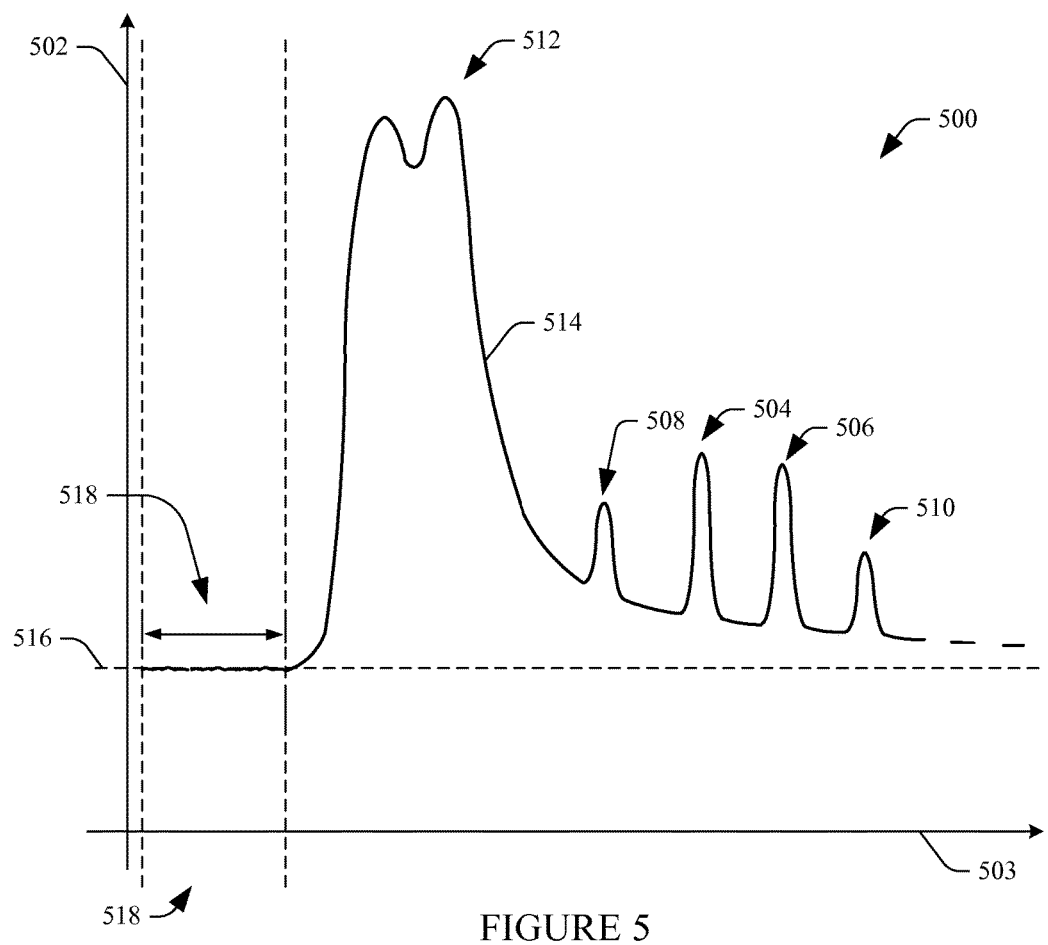
FIG. 5 illustrates an example output signal of a detection channel, similar to that in FIG. 1.

The optical reader 410 also includes an optical detection channel (e.g., a photo-multiplier tube (PMT), a charge-coupled device (CCD) camera, or the like) for each principle emission spectrum range of interest. Each detection channel detects fluorescence light, which is emitted from the dyes in the fragments in response to the dyes being illuminated by the excitation light beam and which is within its principle emission spectrum range, and generates an electrical signal in proportion to the intensity of the detected emission spectrum. Briefly turning to FIG. 5, an example output signal 500 of one of the detection channels for one of the dyes is shown. In FIG. 5, a y-axis 502 represents amplitude and an x-axis 503 represents time.

The output signal 500 includes a set of peaks 504 and 506 (two shown in this example) corresponding to dyes attached to fragments and having principle emission spectra in the emission spectrum range of the detection channel, and peaks 508 and 510 corresponding to other dyes attached to other fragments and having principle emission spectra in the emission spectrum range of one or more other detection channels and emission spectra of the detection channel. The output signal 500 further includes a cluster peak 512, which is a summation of free-dye peaks, which are the peaks for dyes that are not attached to any fragment. As shown, the cluster peak 512 includes a tail 514 that adds to and raises the amplitudes of the peaks 504-510. The tail represents a time-variant offset or baseline of the peaks 504-510.

The output signal 500 also includes a generally time-invariant offset signal 516, which raises the amplitudes of the cluster peak 512 and the peaks 504-510. The time-invariant offset signal 516 is a summation of an offset signal of the optical reader 410 and a background signal including a fluorescent emission signal from the material of the sample carrier 404 and non-fluorescent emission signal of scattered excitation light. Generally, the amplitude of offset signal 516 of the reader 410 is relatively large and can exceed the amplitude of the peaks 504-510, and the amplitude of the offset signal 516 is relatively small. These signals are generally constant (or vary only slightly) during data acquisition.

Figure 6:
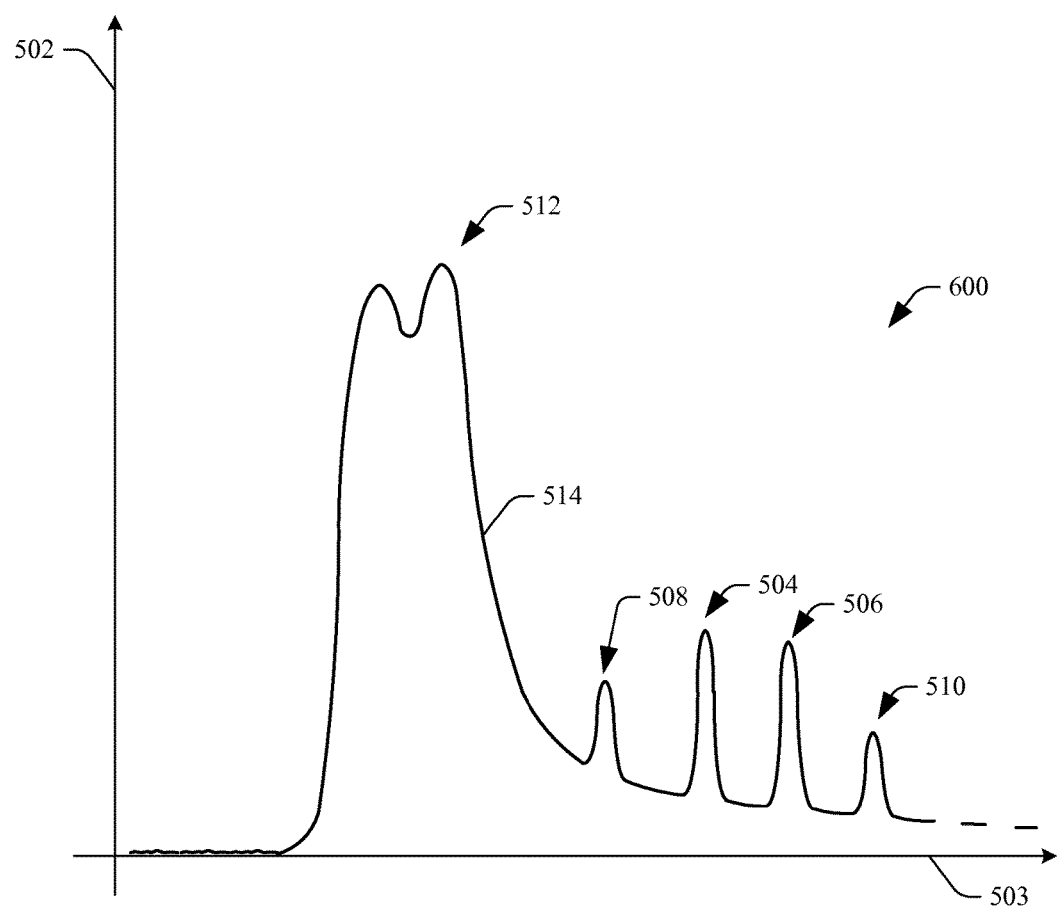
FIG. 6 illustrates the output signal of FIG. 5 with the offset and background signals removed.

With continuing reference to FIGS. 4 and 5 and with reference to FIG. 6, a time-invariant offset signal determiner 412 determines an (average) amplitude of the time-invariant offset signal 516 during a predetermined time duration 518 of data acquisition before the cluster peak 512 arrives. Generally, the time-invariant offset signal 516 can be readily measured with good accuracy. A time-invariant offset signal remover 414 removes (e.g., subtracts) the determined time-invariant offset signal amplitude from the output signal 500 and generates a time-invariant offset corrected signal. FIG. 6 shows an example time-invariant offset corrected signal 600.

Figure 7:
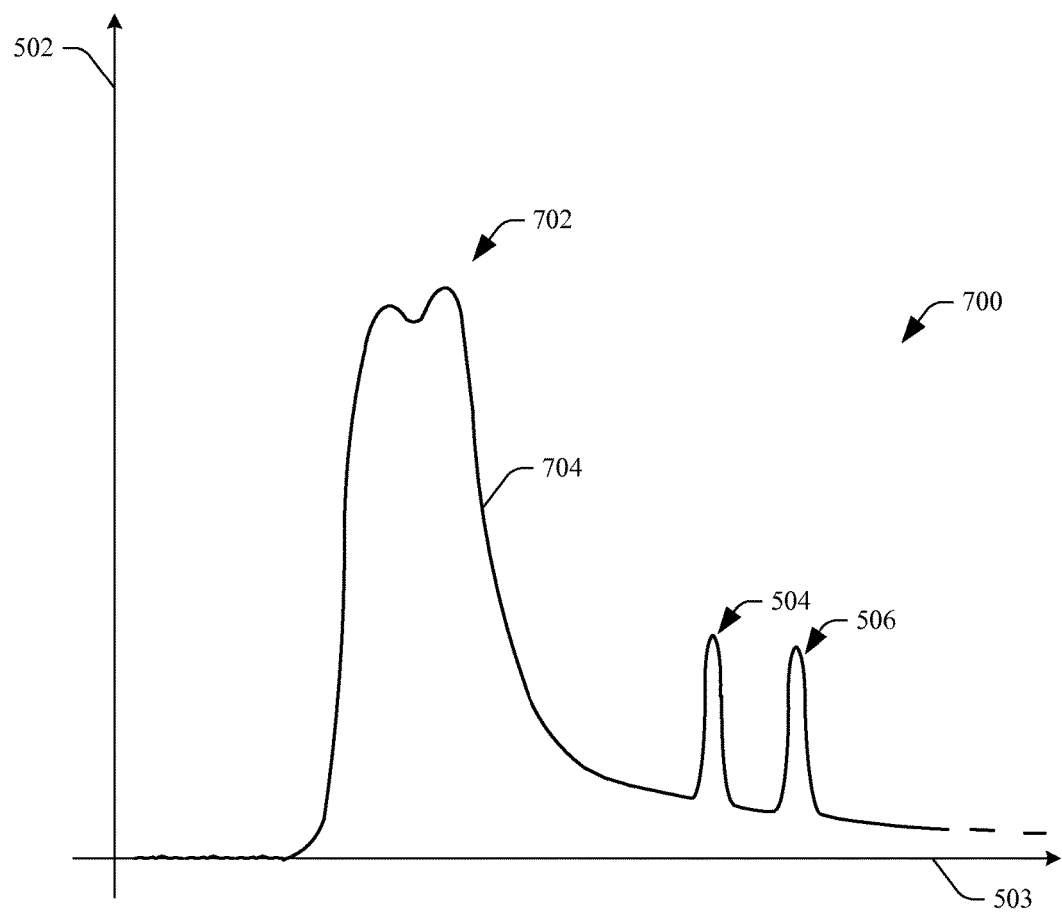
FIG. 7 illustrates an example color-separated output signal for the signal of FIG. 6.

With continuing reference to FIGS. 4 and 6 and with reference to FIG. 7, a color separator 416 color-separates the time-invariant offset corrected signal 600, including the peaks 504-510 and the cluster peak 512. The color separator 416 uses a set of color bleed factors to color-separate the time-invariant offset corrected signals for all the detection channels so that each signal includes peaks corresponding to the spectrum of only one of the dyes. Color bleed factors, including an approach to calibrating and correcting them, are described in PCT application serial number PCT/US2010/53346, filed Oct. 20, 2010, and entitled "Method of Calibrating and Correcting Color-bleed Factors for Color Separation in DNA Analysis," which is incorporated by reference herein in its entirety. FIG. 7 shows an example color-separated signal 700 for one of the detection channels. The signal 700 includes the peaks 504 and 506 and a portion 702 of the cluster peak 512 with emission spectra corresponding to the detection channel including a tail 704. In the illustrated example, the fragment peaks 504 and 506 and the portion 702 are color separated without introducing pull-up artifacts.

Figure 8:
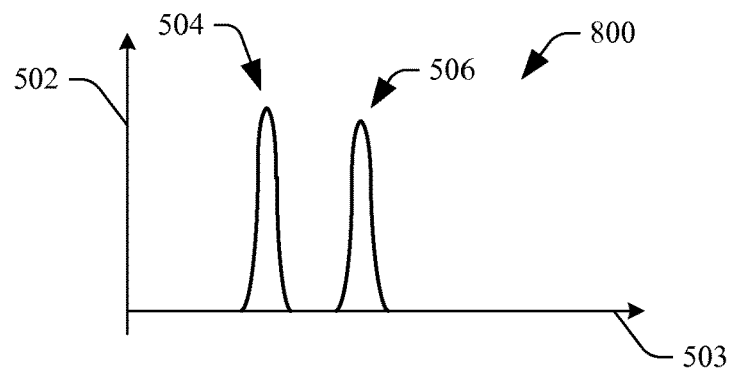
FIG. 8 illustrates the color-separated output signal of FIG. 7 with the cluster removed.

With continuing reference to FIGS. 4 and 7 and with reference to FIG. 8, a time-variant baseline signal determiner 418 determines an amplitude of the tail 704 of the portion 702 of the cluster peak 512 as a function of time. Various techniques can be used to determine the amplitude. For example, the amplitude can be determined as a baseline curve after color separation. In another instance, the time-variant baseline signal determiner 418 determines an amplitude of the cluster peak 512 including the tail 704. A time-variant baseline signal remover 420 removes (e.g., subtracts) the determined amplitude of the time-variant offset signal from the color-separated signal as a function of time and generates time-corrected color-separated signals.

FIG. 8 shows an example corrected color-separated signal 800 for one of the detection channels. As shown, the corrected color-separated signal 800 includes only the fragment peaks 504 and 506. The corrected color-separated color 800 has a flat baseline at zero amplitude. Note that any error in determining and/or removing the time-variant offset signal does not introduce pull-up artifact into the signal 800.

Figure 9:
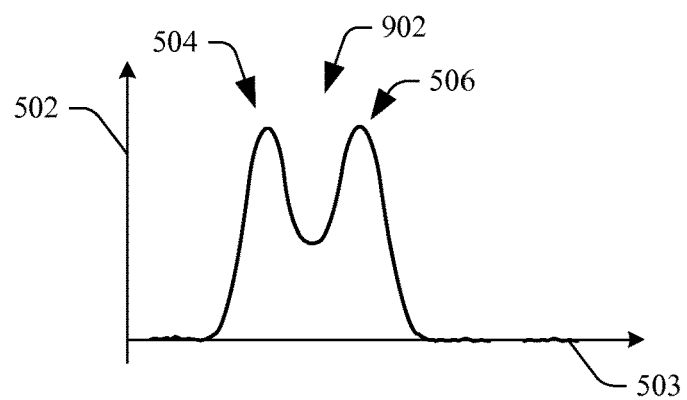
FIG. 9 illustrates an example in which the color-separated signals partially overlap.
Figure 10:
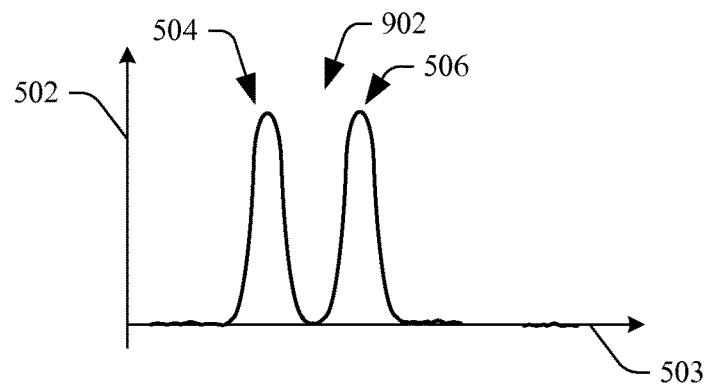
FIG. 10 illustrates an example in which the partially overlapped signal of FIG. 9 are filtered to separate the partially overlapped color-separated detection signal.

With reference to FIG. 9, an optional filter 422 is used to high-pass filter corrected color-separated signals. Such filtering can reduce overlap between peaks. By way of example, in FIG. 9, the peaks 504 and 506 overlap in a region 902. Each peak 504 and 506 diminishes on both sides at about a same rate and can be approximated by a Gaussian function. FIG. 10 shows the peaks 504 and 506 of FIG. 9 after filtering. As shown, the peaks 504 and 506 no longer overlap in the region 902. Generally, the signal shape is the result of convolving a peak shape with a narrow single-point peak. Overlapped peaks can be separated by de-convoluting the signal with the peak shape. The de-convolution is equivalent to the operation of the high-pass filtering. In an alternative embodiment, the high-pass filtering is performed prior to color separation, and, as both of the operations are linear operations, the filtering will lead to the same result. In another embodiment, the filter 422 is omitted.

A STR determiner 424 identifies the peaks in the corrected color-separated signals and determines STR numbers in loci of interest based on the identified peaks. It is to be appreciated that by mitigating the introduction of pull-up artifact during color separation, as described herein, allows for accurately identifying DNA allele numbers, given an accurate set of color bleed factors.

Generally, the above described configuration takes into consideration that the peaks of the free dyes in the cluster peak have the same emission spectra as the fragment peaks, and, instead of removing them before color separation, they are retained to undergo color separation together with the fragment peaks. The offset and background signals, which are essentially time-invariant, are accurately measured and removed.

As a result, color separation can be performed accurately with introducing pull-up artifact. After color separation, the time-variant tail of the cluster peak (or the entire cluster peak) is measured and removed from the color-separated signal for subsequent processing. The foregoing allows for mitigating pull-up artifacts in the color-separated signal, relative to a configuration in which the time-variant tail, which is difficult to measure accurately, is removed before color separation.

Figure 11:
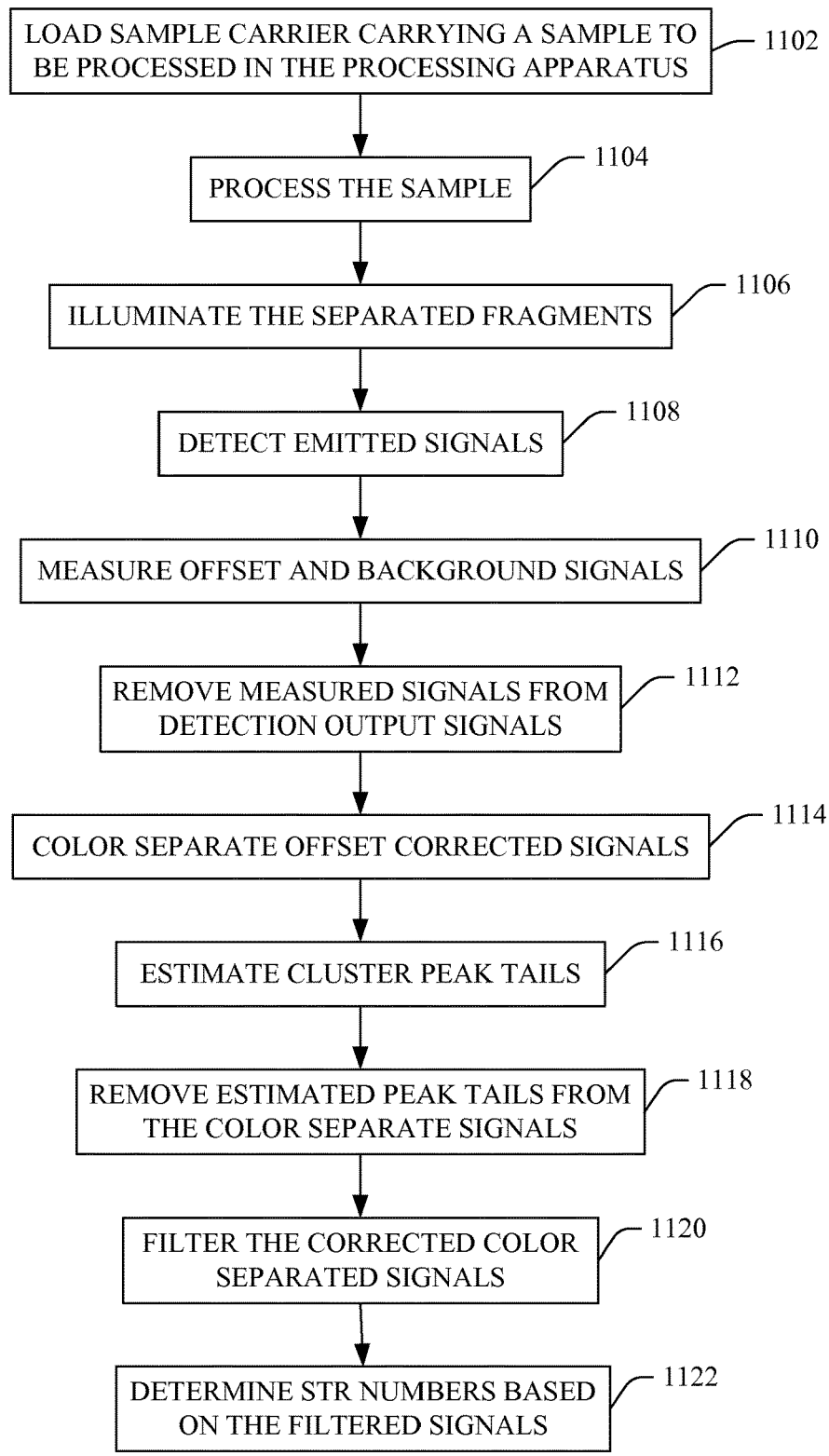
FIG. 11 illustrates an example method for color separating multiple color signals while mitigating pull-up artifact.

FIG. 11 illustrates a method for color separating multiple color signals without introducing pull-up artifact.

It is to be appreciated that the following acts are provided for explanatory purposes and are not limiting. In other embodiments, one or more of the acts are omitted and/or one or more acts are added. In addition, the ordering of the acts may be different and/or certain acts can occur concurrently.

At 1102, a sample carrier carrying a sample is loaded in a sample processing apparatus.

At 1104, the sample is processed by one or more processing stations of the sample processing apparatus. This may include one or more of extracting and purifying a DNA fragment, replicating the fragment, labeling the fragments using nucleotide specific fluorescent dyes, or separating the labeled fragments by fragment size, as described herein.

At 1106, the separated fragments are illuminated with an excitation light source.

At 1108, emissions from the dyes in response to the illumination are detected by a plurality of detections channels, each channel being configured to detect a signal corresponding to the emission spectrum of a particular one of the dyes.

As discussed herein, the output signal of each detection channel will include peaks corresponding to dyes of fragments with principle emission spectra in the spectrum of the detection channel, peaks corresponding to other dyes of the fragments with principle emission spectra in the spectrum of at least one other detection channel and emission spectra in the spectrum of the detection channel, a cluster peak with a tail that adds a baseline that raises the peaks, and offset and background signals.

At 1110, the offset and background signals of each detection signal are measured. As discussed herein, the offset and background signals are generally amplitude time-invariant signals that add to and raise the peaks and cluster peaks.

At 1112, the measured signals are removed from the corresponding detection signals. As discussed herein, this can be achieved by subtracting the measured offset and background signals from the corresponding detection signals.

At 1114, the offset corrected detection signals are color-separated. As discussed herein, color separating a detection signal removes peaks and free dye peaks having principle emission spectra not corresponding to the detection channel.

At 1116, a time-variant amplitude of the tail of the cluster of free dye peaks for each of the detection signal is estimated. Alternatively, a time-variant amplitude of the cluster peak is estimated.

At 1118, the estimated amplitudes are removed from the corresponding color-separated signals.

At 1120, the color-separated signals is high pass filtered. As discussed herein, this can facilitate separating partially overlapping peaks. Alternatively, this filtering can be performed before the color separating.

At 1122, the filtered color-separated signals are used to determine STR numbers for the DNA sample and identify DNA allele numbers.

It is to be appreciated that the methods herein can be implemented via one or more processors of one or more computing systems executing one or more computer readable and/or executable instructions stored on computer storage medium such as memory local to or remote from the one or more computing systems. Additionally or alternatively, the processor can execute one or more computer readable and/or executable instructions carried in a single or carrier wave.

The following describes embodiments herein in another manner.

The fluorescent light intensity from a dye i is $X_i$ and the light intensity detected through a detector channel j is $Y_j$. The acquired signal from each detection channel contains substantial amount of offset and certain amount of background signal. The background signal is mostly the excitation light scattered by the biochip material surrounding the capillary. The amount of these offset and background signal are fairly constant throughout the data acquisition, and can be calculated and used for baseline correction.

The variable $Y_j$ is the signal amplitude after the baseline has been subtracted from the acquired signal. For an example with five (5) dyes and five (5) detection channels, the detected signal for channel j can be written as the combination of fluorescent light from five (5) dyes as shown in Equation 1:

$$Y_j = A_{j1}*X_1 + A_{j2}*X_2 + A_{j3}*X_3 + A_{j4}*X_4 + A_{j5}*X_5. \quad \text{Equation 1:}$$

The coefficient $A_{ji}$ can be considered as the color-bleed factor from dye i to detection channel j, if i is not the same as j. For the case of i=j, the coefficient $A_{ii}$ represents the detection efficiency of a dye by its principle channel. It is the principle coefficient, which has the largest value.

The color bleed effect can be described through Equation 2:

$$Y_j = \sum_{i=1}^{5} A_{ji} * X_i \quad \text{Equation 2}$$

with $j = 1, 2, \ldots, 5$.

If X is the vector of the dye emission intensities, Y is the vector of the detected signal amplitudes, and A is the matrix of the color-bleed factors, the foregoing can be written as a matrix operation as shown in Equation 3:

$$Y = AX. \quad \text{Equation 3:}$$

Equation 3 describes the relationship between the dye emission intensity and the detected signal amplitude in a set of simultaneous equations. The unknown dye emission intensity X can be solved by using the inverse matrix of A., as shown in Equation 4:

$$B = A^{-1}. \quad \text{Equation 4:}$$

Then, the dye emission intensity X is given by Equation 5:

$$X = BY, \quad \text{Equation 5:}$$

and in expanded terms as shown in Equation 6:

$$X_i = \sum_{j=1}^{5} B_{ij} * Y_j. \qquad \text{Equation 6}$$

While the color-bleed factors $A_{ji}$ are all positive values, the inverse matrix coefficients $B_{ij}$ can be positive and negative values.

The calculation for the dye emission intensities can be considered as de-convolution of the detected signal amplitudes. If the actual color-bleed factors are not accurate or if the signal amplitude $Y_j$ is not measured accurately, the color separation will contain noticeable errors (pull-up and negative pull-up (or pull-down)). These errors are artifacts in the signal for the subsequent processing and add uncertainty to the detection and identification of DNA fragments in the sample.

Recall that the output signal of each of the detection channels includes fluorescent fragment peaks, fluorescent free-dye peaks with a time-variant tail, and time-invariant offset and background signals.

In order to avoid or reduce the pull-up artifact, the color-bleed factors $A_{ji}$ should be accurately prepared. These factors should remain unchanged and accurate during the detection of DNA samples. Secondly, the offset and background signals should be accurately calculated. They are used to obtain the signal $Y_j$ from the DNA fragments, by subtracting it from the acquired signal.

After the subtraction, the signal amplitude $Y_j$ still includes the free dye cluster peak, along with its gradual diminishing tail, and the fluorescent fragment peaks. All of these components in the signal $Y_j$ are emitted from the same fluorescent sources, and they have the same the color-bleed factors $A_{ji}$. These components can be separated by the inverse matrix coefficients $B_{ij}$, without introducing pull-up artifacts.

After the color separation, each signal contains the fragment peaks from the principle color as well as the peaks from the free dye of the principle color and its gradual diminishing tail, which are well preserved in the input variable $Y_j$. The cluster peak can then be removed, and the resulting signal is used for subsequent analysis, STR determination, and DNA allele number identification.

From the above, the time-invariant signals are measured for each detection channel output signal and subtracted therefrom. The signal, which still includes the peaks, is then color separated. The resulting signal includes the peaks corresponding to the detection channel and the portion of the free-dye cluster peak corresponding to the detection the detection channel. The tail or cluster is the estimated and removed from the color-separated signals. Optionally, the resulting signals can be high-pass filtered facilitate separating partially overlapping peaks. The resulting signal is used for subsequent DNA analysis.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method of color separating peaks, the method comprising:
   directing emitting of an excitation beam at a DNA fragment in a sample carrier inserted into a receptacle of a sample processing system;
   detecting emission spectra in different predetermined emission spectrum ranges using multiple detection channels and generating output signals indicative thereof;
   receiving an output signal from a detection channel of the multiple detection channels, wherein the output signal includes peaks corresponding to detected signals with principle emission spectra in the emission spectrum range of the detection channel and peaks corresponding to detected signals with principle emission spectra in the emission spectrum range of one or more other of the detection channels and with emission spectra that overlaps the emission spectrum range of the detection channel;
   color-separating the output signal and generating a color-separated signal substantially only with the peaks corresponding to the detected signals with the principle emission in the emission spectrum range of the detection channel, wherein the color-separated signal includes peaks corresponding to fluorescent dyes attached to fragments in a DNA sample and a cluster peak corresponding to fluorescent dyes that are not attached to fragments in the sample, and wherein the cluster peak includes a gradually decaying tail with a time-variant amplitude that adds to and raises amplitudes of the peaks corresponding to the fluorescent dyes attached to the fragments in the sample;
   estimating the time-variant amplitude of the gradually decaying tail by determining an amplitude of the cluster peak including the time-variant amplitude of the gradually decaying tail; and
   removing the time-variant amplitude from the color-separated signal by removing the determined amplitude of the cluster peak, which generates a corrected color-separated signal with only the peaks corresponding to the fluorescent dyes attached to the fragments in the sample.

2. The method of claim 1, further including:
   prior to color-separating, determining a time-invariant amplitude of offset and background signals of the output signal, wherein the amplitude of the time-invariant offset and background signals adds to and raise amplitudes of the peaks and the cluster peak in the output signal, and removing the time-invariant amplitude from the output signal and generating an offset and background corrected output signal; and
   color-separating the offset and background corrected output signal and generating the color-separated signal substantially only with the peaks corresponding to the detected signals with the principle emission in the emission spectrum range of the detection channel.

3. The method of claim 2, wherein the color-separated signal includes no or substantially no pull-up artifact from the peaks corresponding to the signals with the principle emission in the one or more other of the detection channels.

4. The method of claim 2, wherein the offset signal corresponds to at least one of an illumination source that emits an excitation signal that invokes emission of the detected signals or the detection channel.

5. The method of claim 4, wherein the background signal corresponds to at least one of an emission of a material of a sample carrier carrying the sample in response to being illuminated by the excitation signal or scatter excitation signal.

6. The method of claim 2, wherein the time-invariant amplitude is determined as an average amplitude of a region of the output signal before the cluster peak.

7. The method of claim 1, wherein the output signal includes partially overlapped peaks, and further comprising: high-pass filtering the output signal to separate the partially overlapped peaks, wherein the color-separating includes color-separating the filtered output signal.

8. The method of claim 1, wherein the corrected color-separated signal includes partially overlapped peaks, and further comprising: high-pass filtering the corrected color-separated signal to separate the partially overlapped peaks.

9. The method of claim 1, further comprising:
identifying a human subject from which the DNA is from by determining STR numbers from the corrected color-separated signal, identifying DNA allele numbers from the STR numbers, and identifying a human from which the DNA originates from the DNA allele numbers.

10. A computer-readable storage medium with computer-executable instructions embedded thereon, which, when executed by a processor of an apparatus configured to sequence DNA, cause the processor to:
color-separate fluorescent-dye-labeled DNA fragments of a DNA sample, which were separated by size through electrophoresis, by:
controlling a light source of an optical reader of the sample processing system to emit an excitation light beam and direct the emitted excitation light beam at the DNA sample;
detecting, with each of a plurality of detection channels of the optical reader, fluorescence light emitted from the dyes in response to illumination of the dyes by the excitation light beam; and
generating, with the detection channels, output signals that each include an electrical signal in proportion to an intensity of an emission spectrum of the detected fluorescence light;
measuring an amplitude of a time-invariant offset to the output signals by determining an average amplitude of a summation of an offset signal of the optical reader and a background signal during a predetermined time duration;
removing the measured amplitude of the time-invariant offset from the output signals by removing the average amplitude, generating time-invariant offset-corrected signals; and
color-separating the time-invariant offset-corrected signals using a predetermined set of color-bleed factors, generating a plurality of color-separated signals in which each color-separated signal corresponds to a spectrum of one dye;
correct the plurality of color-separated signals with the apparatus by:
estimating a time-variant offset to the color-separated signals by determining a baseline curve of the color-separated signals; and
removing the determined amplitude of the time-variant offset from the color-separated signals by subtracting the determined baseline curve from the color-separated signals as a function of time, generating a plurality of corrected color-separated signals; and
determine STR numbers for the DNA sample with the corrected color-separated signals and identify DNA allele numbers from the STR numbers.

11. The computer-readable storage medium of claim 10, wherein the DNA allele numbers identify a human from which the DNA sample is acquired.

12. The computer-readable storage medium of claim 10, wherein the color-separated signal includes no or substantially no pull-up artifact.

13. The computer-readable storage medium of claim 10, wherein the computer-executable instructions, when executed by the processor, further causes the processor to: high-pass filter the time-invariant offset-corrected signal before color-separating the time-invariant offset-corrected signal or high pass filtering the corrected color-separated signal.

14. A method, comprising:
labeling DNA fragments with fluorescent dyes to form dye-labeled separated fragments of DNA;
directing an excitation light beam at a sample comprising the dye-labeled separated fragments to illuminate at least some of the dyes;
detecting fluorescent light emitted from the dyes in the dye-labeled separated fragments in response to the dyes being illuminated by the excitation light beam;
generating an electrical signal having an intensity indicative of the detected fluorescence light;
color-separating the electrical signal to generate a color-separated signal;
estimating a time-variant amplitude of a gradually decaying tail of an electrical output signal;
removing the time-variant amplitude from the color-separated signal to generate a corrected color-separated signal; and
determining STR numbers for a DNA sample with the corrected color-separated signal.

15. The method of claim 14, wherein estimating the time-variant amplitude of the gradually decaying tail comprises determining a baseline curve of the color-separated signal.

16. The method of claim 15, wherein removing the time-variant amplitude from the color-separated signal comprises subtracting the determined baseline curve from the color-separated signal as a function of time.

17. The method of claim 14, wherein estimating the time-variant amplitude of the gradually decaying tail includes determining an amplitude of a cluster peak that includes the gradually decaying tail, wherein the cluster peak is a summation of free-dye peaks, which are peaks for dyes not attached to any fragment in the DNA sample.

18. The method of claim 17, wherein removing the time-variant amplitude from the color-separated signal comprises subtracting the determined amplitude of the cluster peak from the color-separated signal.

19. The method of claim 14, wherein estimating the time-variant amplitude of the gradually decaying tail comprises measuring a time-variant tail of a cluster peak.

20. The method of claim 19, wherein removing the time-variant amplitude from the color-separated signal comprises subtracting the measured time-variant tail of the cluster peak from the color-separated signal.

21. The method of claim 14, wherein estimating the time-variant amplitude of the gradually decaying tail comprises measuring a cluster peak, which is a summation of free-dye peaks, which are peaks for dyes not attached to any fragment in the DNA sample.

22. The method of claim 21, wherein removing the time-variant amplitude from the color-separated signal comprises subtracting the entire cluster peak from the color-separated signal.

23. The method of claim 14, wherein removing the time-variant amplitude from the color-separated signal comprises subtracting the time-variant amplitude from the color-separated signal as a function of time.

* * * * *

UNITED STATES PATENT AND TRADEMARK OFFICE
CERTIFICATE OF CORRECTION

PATENT NO. : 10,401,288 B2
APPLICATION NO. : 13/076576
DATED : September 3, 2019
INVENTOR(S) : Ching Ming Lai Page 1 of 1

It is certified that error appears in the above-identified patent and that said Letters Patent is hereby corrected as shown below:

On the Title Page
In ITEM (57) ABSTRACT,   Line 10   change "corrected colored-separated" to --corrected color-separated--

In the Specification
Column 3,   Lines 46,47   change "corrected colored-separated" to --corrected color-separated--

Signed and Sealed this
Twenty-second Day of October, 2019

Andrei Iancu
*Director of the United States Patent and Trademark Office*